(12) United States Patent
Merz et al.

(10) Patent No.: US 10,548,577 B2
(45) Date of Patent: Feb. 4, 2020

(54) HANDLING DEVICE FOR A MEDICAL INSTRUMENT

(71) Applicant: Karl Storz SE & Co. KG, Tuttlingen (DE)

(72) Inventors: Robin Merz, Furtwangen (DE); Sven Schneider, Tuttlingen (DE); Jochen Stefan, Wald (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 1835 days.

(21) Appl. No.: 13/865,532

(22) Filed: Apr. 18, 2013

(65) Prior Publication Data

US 2013/0304041 A1  Nov. 14, 2013

(30) Foreign Application Priority Data

Apr. 18, 2012 (DE) .................. 10 2012 007 650

(51) Int. Cl.
| | | |
|---|---|---|
| *A61B 17/00* | (2006.01) | |
| *A61B 17/29* | (2006.01) | |
| *F16H 21/44* | (2006.01) | |
| *A61B 18/14* | (2006.01) | |

(Continued)

(52) U.S. Cl.
CPC .... *A61B 17/00234* (2013.01); *A61B 17/2909* (2013.01); *A61B 18/1445* (2013.01);
(Continued)

(58) Field of Classification Search
CPC .......... A61B 17/00234; A61B 17/2909; A61B 17/295; A61B 2017/0046;
(Continued)

(56) References Cited

U.S. PATENT DOCUMENTS

| | | | |
|---|---|---|---|
| 5,342,391 A | | 8/1994 | Foshee et al. |
| 5,913,874 A | * | 6/1999 | Berns .................. A61B 17/295 |
| | | | 606/205 |

(Continued)

FOREIGN PATENT DOCUMENTS

| | | |
|---|---|---|
| DE | 19852682 A1 | 5/2000 |
| DE | 602005001056 T2 | 1/2008 |

OTHER PUBLICATIONS

European Search Report Application No. EP 13 00 1867 Completed: Aug. 24, 2015; dated Sep. 4, 2015 7 pages.

*Primary Examiner* — Erich G Herbermann
(74) *Attorney, Agent, or Firm* — Whitmyer IP Group LLC

(57) ABSTRACT

A handling device for a medical instrument includes a main body with a coupling for releasable mechanical connection to a proximal end of an outer shaft, a first actuation device movable relative to the main body, a second actuation device movable relative to the main body, a first coupling device coupling the first actuation device to a first transfer device for transferring at least a force or a torque, and a second coupling device coupling the second actuation device to a second transfer device for transferring at least a force or a torque. The coupling devices each have a decoupling position, in which the associated actuation device is decoupled from the associated transfer device. The decoupling positions of both coupling devices can only be reached when the outer shaft is not connected to the coupling on the main body in the manner provided for use of the medical instrument.

18 Claims, 5 Drawing Sheets

(51) Int. Cl.
*A61B 17/3201* (2006.01)
*A61B 17/295* (2006.01)
*A61B 18/00* (2006.01)

(52) U.S. Cl.
CPC ............ *F16H 21/44* (2013.01); *A61B 17/295* (2013.01); *A61B 17/3201* (2013.01); *A61B 2017/0046* (2013.01); *A61B 2017/00464* (2013.01); *A61B 2017/292* (2013.01); *A61B 2017/2912* (2013.01); *A61B 2017/2925* (2013.01); *A61B 2018/0091* (2013.01); *A61B 2018/1455* (2013.01); *Y10T 74/1892* (2015.01)

(58) Field of Classification Search
CPC .. A61B 2017/00464; A61B 2017/2912; A61B 2017/292; A61B 2017/2946; A61B 2017/294; A61B 2017/2938; A61B 10/06; A61B 18/1445; A61B 17/3201; A61B 2017/2925; A61B 2018/0091; A61B 2018/1455

USPC ....... 606/167, 205–207, 169–180; 227/175.1
See application file for complete search history.

(56) References Cited

U.S. PATENT DOCUMENTS

| | | | |
|---|---|---|---|
| 6,358,267 B1 | 3/2002 | Murakami et al. | |
| 7,101,372 B2* | 9/2006 | Dycus ................ | A61B 18/1445 606/205 |
| 7,717,932 B2* | 5/2010 | McFarlin ........... | A61B 17/1622 606/170 |
| 2003/0032954 A1* | 2/2003 | Carranza .............. | A61B 18/148 606/41 |
| 2005/0021079 A1* | 1/2005 | Kalmann ................ | A61B 17/29 606/205 |
| 2010/0312240 A1* | 12/2010 | Boulnois ........ | A61B 17/320016 606/48 |

* cited by examiner

HANDLING DEVICE FOR A MEDICAL INSTRUMENT

FIELD OF THE INVENTION

The present invention is based on a handling device for a medical instrument and on a medical instrument, in particular on the releasable mechanical coupling of the handling device to transfer devices in a shaft.

BACKGROUND OF THE INVENTION

The expectations of medical instruments, in particular of medical instruments for microinvasive interventions, increase continuously. A variety of medical instruments comprising a tool with gripping or cutting function at the distal end are already offered and are widespread. Further functions and degrees of freedom are increasingly added, for example a rotation of the tool about the longitudinal axis of the shaft, a bending capacity of the shaft proximally of the tool, or a second, independently controllable active device on the tool. In order to control these further functions or degrees of freedom, a second transfer element may be provided in the shaft of the medical instrument, for example a second transfer rod.

In the case of reusable medical instruments, it is necessary for cleaning purposes to be able to disassemble said instruments to the greatest possible extent. In the case of many medical instruments, the handling device in particular is separable from the proximal end of the shaft. Here, a snap-in connection between the proximal end of the shaft or the outer shaft on the one hand and the handling device on the other hand can be unlocked by applying manual pressure to an unlocking button or by actuating another actuation device. In the case of medical instruments produced by the applicant and distributed under the name "Clickline", as the shaft is removed distally from the handling device the proximal end of the transfer rod and a lever coupled thereto of the holding device reach positions in which they are no longer coupled to one another. The coupling between the proximal end of the transfer rod and the handling device or a lever on the handling device is therefore releasable when the coupling between the proximal end of the shaft and the handling device is released.

The releasability or separability known from "Clickline" products of the proximal ends of the outer shaft and of the transfer rod on the one hand from the handling device on the other hand cannot however be transferred to many other medical instruments, or cannot be transferred easily, in particular if more than one independently movable transfer device is arranged in the outer shaft. An alternative lies in providing a separate actuation device for each coupling. In the case of a medical instrument having an outer shaft and two transfer rods or other transfer devices, three actuation devices are therefore to be provided, wherein a respective coupling between the proximal end of the outer shaft or a transfer rod on the one hand and the handling device on the other hand can be released by means of manual actuation of said actuation devices.

SUMMARY OF THE INVENTION

The object of the present invention is to create an improved handling device for a medical instrument and an improved medical instrument.

This object is achieved by the subjects of the independent claims.

Further developments are disclosed in the dependent claims.

Exemplary embodiments of the present invention are based on the concept of forming on a handling device a plurality of coupling devices for releasable mechanical coupling of a respective associated actuation device to an associated transfer device in an outer shaft to be connected to the handling device, such that each coupling device has an associated decoupling position, in which the associated actuation device is decoupled the associated transfer device, wherein the decoupling positions of the coupling devices can then only be reached when the outer shaft in not connected in the provided manner to the handling device.

Under consideration of the "Clickline" products mentioned in the introduction, the impression has been created that the automatic coupling and decoupling to be observed in that instance between the proximal end of the transfer rod and a lever-shaped actuation device cannot be transferred to medical instruments having two or more transfer devices. In particular, the releasable mechanical coupling of the transfer rod, which is provided to pivot one or two mouth parts, to a lever-shaped actuation device in the case of the "Clickline" products constitutes a special case in so far as this lever-shaped actuation device can be easily biased or moved by a spring into the position in which a coupling and decoupling of transfer rod and actuation device is possible. This is because this position corresponds to an open position or arrangement of mouth parts on the tool at the distal end of the shaft. In the case of other functions and degrees of freedom, a preference of a specific position or arrangement by means of spring force is generally undesirable.

The variants and exemplary embodiments described here demonstrate that a trivial transfer of the coupling, known from the "Clickline" products, between the transfer rod and the associated actuation device to the coupling between further transfer devices and associated actuation devices cannot actually be easily implemented, but additional design features are necessary. Fortunately, similarly simple handling when assembling and disassembling a medical instrument is then possible however.

A handling device for a medical instrument comprises a main body with a coupling for releasable mechanical connection to a proximal end of an outer shaft, a first actuation device, which is movable relative to the main body, a second actuation device, which is movable relative to the main body, a first coupling device for coupling the first actuation device to a first transfer device for transferring at least either a force or a torque, and a second coupling device for coupling the second actuation device to a second transfer device for transferring at least either a force or a torque, wherein the first coupling device and the second coupling device each have a decoupling position, in which the associated actuation device is decoupled from the associated transfer device, and wherein the decoupling positions of both coupling devices can then only be reached when the outer shaft is not connected to the coupling on the main body in the manner provided for the use of the medical instrument.

The handling device is provided and designed in particular for a microinvasive surgical instrument or to form a microinvasive surgical instrument consisting of the handling device, a tool, and an outer shaft, which receives the first actuation device and the second actuation device. Here, the first transfer device in particular is a transfer rod, and the second transfer device in particular is an inner shaft, wherein the inner shaft and the transfer rod are arranged coaxially in the outer shaft. The outer shaft and transfer devices may each be straight or curved, rigid or flexible. The transfer devices in particular are each designed to transfer at least either a force or a torque to an associated tool at the distal end of the shaft, to pivot a mouth part, or to move a blade or scalpel.

The main body of the handling device may be designed in one or more parts. The first actuation device and the second actuation device are each pivotable or movable in translation, in particular relative to the main body. The first actuation device is designed for example to control the opening and closing of gripping or cutting mouth parts. The second actuation device is designed for example to control the movement of a scalpel.

In the configuration of the medical instrument usable in medical interventions, the outer shaft is connected in a provided manner to the main body, in particular is arranged in the provided position relative to the main body and is held in this position by the coupling on the main body. The coupling in particular comprises a recess, of which the geometrical design corresponds to the proximal end of the outer shaft. The coupling can be formed in the manner of a bayonet coupling, or may comprise a thread and/or a bolt for locking the outer shaft in the provided position relative to the main body of the handling device.

In particular, the first coupling device can then adopt its associated decoupling position and the second coupling device can then adopt its associated decoupling position when the outer shaft is separated from the main body of the handling device or is sufficiently spaced from the position in which it can be mechanically connected releasably, yet rigidly, to the coupling on the main body.

In the case of a handling device as is described here, the second coupling device in particular is electrically insulated in any position at least either from the proximal end of an outer shaft connected to the handling device or from the proximal end of a first transfer device coupled to the first actuation device.

The electrical insulation of the second coupling device from the proximal end of the outer shaft having an electrically conductive surface and/or from the proximal end of the first transfer device having an electrically conductive surface in particular includes the fact that sufficient creeping distances are present for the electrical voltages conventional in electrosurgery or for electrocauterisation.

The fact that the second coupling device is electrically insulated in any position from the proximal end of the outer shaft and/or from the proximal end of the first transfer device enables a use of the handling device for a bipolar electrosurgical instrument, in which the outer shaft and the first transfer device are connected to two different poles or are provided for transfer of the two different electric potentials. A transfer rod or an inner shaft may often be easily insulated externally by means of a stocking tube. At the proximal end, a transfer rod or an inner shaft often has blank metal surfaces however, which, due to their hardnesses and their wear properties, are particularly suitable for mechanical coupling to the associated coupling device of the handling device. The same applies accordingly for the coupling on the main body and for the coupling devices of the handling device: these generally have metal and therefore electrically conductive surfaces due to the desired hardnesses and due to the desired wear properties. The electrical insulation provided at all times of the second coupling device from the proximal end of the outer shaft and/or from the proximal end of the first transfer device in particular includes a corresponding electrical insulation of the second coupling device from the coupling on the main body and/or from the first coupling device or from the electrically conductive components thereof in any position of the second coupling device.

In the case of a handling device as is described here, the first actuation device in particular is designed to open and close mouth parts of a first tool, and the second actuation device in particular is designed to move a second tool at the distal end of a shaft to be coupled to the handling device.

The first tool in particular is a pair of tongs, a pair of shears or another gripping or cutting tool comprising two or more mouth parts, of which at least one is pivotable relative to the other mouth part or mouth parts. The first tool in particular is also designed for monopolar or bipolar electrosurgery. The second tool in particular is a blade or scalpel, which is displaceable in the longitudinal direction in a channel between the closed mouth parts of the first tool designed as a pair of tongs. For example, a vessel can therefore be severed after the gripping, squeezing and electrosurgical closing procedures.

In the case of a handling device as is described here, the first actuation device in particular is arranged proximally of a stationary grip part of the handling device, and the second actuation device in particular is arranged distally of the stationary grip part.

In particular, the stationary grip part is arranged at an angle between 50° and 90° with respect to the longitudinal axes of an outer shaft to be connected to the handling device, the first actuation device is pivotable about an axis perpendicular with respect to the longitudinal axis, and the stationary grip part and the first actuation device are designed similarly to the grips of a pair of shears and can be gripped and moved by hand. In particular, the second actuation device comprises a slide, a lever, a pull lever or a push button. The second actuation device is in particular arranged such that it can be easily actuated by the index finger of a hand, of which the other fingers grip the stationary grip part and the first actuation device in the provided manner. A handling device in which the first actuation device is arranged proximally of the stationary grip part and the second actuation device is arranged distally of the stationary grip part may thus have an advantageous similarity in terms of ergonomics and in terms of the handling procedure familiar to medical staff compared to conventional handling devices, in particular those included among the above-mentioned "Clickline" products.

In the case of a handling device as is described here, the second coupling device in particular comprises a carriage, which is displaceable by means of the second actuation device along a predetermined path.

A carriage is in particular a component that is guided by means of sliding bearings and/or rolling bearings on one or more rails or other guide devices, wherein the guide devices define the predetermined path. Apart from play and resilient deformation, the carriage has just one degree of freedom, specifically the movement along the predetermined path. The predetermined path is in particular straight and in particular parallel with respect to the longitudinal axis of the outer shaft and transfer devices, and in the case of a curved outer shaft: parallel with respect to the longitudinal axis of the outer shaft at the proximal end thereof. The decoupling position of the second coupling device is in particular at the distal end of the predetermined path of the carriage, wherein the second coupling device can be designed such that the second transfer device and the second coupling device can be coupled in any position of the coupling device.

The carriage may constitute an option that can be produced easily in terms of construction and manufacture. For example, opposed edges of the carriage or webs or journals or pins or other convex regions on opposite sides of the carriage engage in corresponding grooves on the main body of the handling device. Alternatively, webs on the main body of the handling device may, conversely, engage in grooves on opposite sides of the carriage.

In the case of a handling device as is described here, the second coupling device in particular comprises a bolt for holding the proximal end of the second transfer device in an interlocked manner on the carriage, wherein the main body is designed, as the second coupling device approaches the decoupling position, to move the bolt into an unlocking position, in which the bolt no longer holds the proximal end of the second transfer device in an interlocked manner.

The bolt is in particular arranged on or in the carriage and is guided on the carriage such that it is movable relative to the carriage along a predetermined path.

In the case of a handling device as is described here, the carriage in particular is movable in a first direction and the bolt in particular is movable relative to the carriage in a second direction perpendicular with respect to the first direction.

The first direction is in particular parallel with respect to the longitudinal axis of an outer shaft to be connected to the handling device or with respect to the longitudinal axis at the proximal end thereof. If the first and the second direction are perpendicular with respect to one another, a force acting on the carriage and on the bolt parallel with respect to the first direction, as is necessary for example in order to displace the second transfer device in the outer shaft, may cause no movement of the bolt relative to the carriage and therefore also no decoupling.

In the case of a handling device as is described here, the second coupling device in particular is movable by means of the second actuation device along a curved path.

The curved path along which the second actuation device is movable is in particular a path in the shape of a circular arc, of which the midpoint is defined by the pivot axis of the second actuation device, wherein the second coupling device for example is connected rigidly to the second actuation device or is even formed in one piece therewith, at least in part. In particular, the rigid connection of the second coupling device to the pivotable second actuation device can be produced particularly easily in terms of construction and manufacture.

The decoupling position of the second coupling device is in particular at the distal end of the predetermined path of the carriage. The second coupling device can be designed such that the second transfer device and the second coupling device can be coupled in any position of the coupling device.

In the case of a handling device as is described here, an interlocked coupling of the second coupling device to the second transfer device is dependent in particular on a spacing between the second coupling device and a longitudinal axis of the second transfer device, wherein the decoupling position of the second coupling device over the curved path is distanced so far from the longitudinal axis that there is no coupling between the second coupling device and the second transfer device, and other positions of the second coupling device are arranged so close to the longitudinal axis that an interlocked coupling of the second coupling device to the second transfer device may be present.

Other positions of the second coupling device, in which an interlocked coupling of a second coupling device to the second transfer device may be present, are also referred to as working positions. In working positions also, there is no need for a coupling to be present, since the second coupling device can also adopt these working positions in particular when the handling device is not connected to an outer shaft and transfer devices in an outer shaft.

In the case of a handling device as is described here, the second coupling device in particular comprises a bolt, wherein the bolt is displaceable along the curved path by actuation of the second actuation device, and wherein the bolt is movable relative to the second actuation device along a further path, which is substantially perpendicular with respect to the curved path.

The mechanical coupling between the second coupling device and the second transfer device is achieved in particular by means of the bolt. The further path is straight in particular. The further path is in particular then substantially perpendicular with respect to the curved path when the angle between the curved path and the further path is at least 60° or at least 80°. The coupling of the second coupling device to the second transfer device is achieved in particular by interlocked coupling of journals on the second transfer device to the bolt, for example as a result of the accommodation of journals on the second transfer device in corresponding grooves on the bolt. The second transfer device and the bolt are displaceable relative to one another, in particular parallel with respect to the further path, for example since the aforementioned grooves on the bolt are parallel with respect to the further path.

In the case of a handling device as is described here, the bolt is movable out of a working position, in particular relative to the second actuation device along the further path against a resilient force of a resilient element, wherein the bolt has a sliding surface, which is inclined with respect to the curved path and with respect to the further path and is designed and arranged such that a proximal end, introduced into the handling device, of a second transfer device can slide the bolt along the further path at the sliding surface.

The sliding surface with the aforementioned properties can enable a displacement of the bolt by means of simple insertion of the proximal end of the second transfer device into the handling device. Here, the bolt can reach a coupling position, in which the second transfer device is coupled to the second coupling device, for example by transferring the bolt from the coupling position back into the working position, driven by the resilient element. The sliding surface with the described properties can enable a coupling of a second transfer device to the second coupling device in working positions of the second coupling device.

In the case of a handling device as is described here, the second coupling device is designed in particular such that the second transfer device is rotatable about its longitudinal axis relative to the second coupling device.

A handling device as is described here may have a spring or another resilient element, which is coupled to the second actuation device in such a way that it moves the second actuation device into a predetermined position.

A medical instrument has a handling device as is described here and a shaft, which comprises an outer shaft and in the outer shaft a first transfer device and a second transfer device.

In the case of a medical instrument as is described here, the proximal end of the outer shaft prevents the second coupling device form reaching its decoupling position when the outer shaft is connected to the main body in the provided manner.

The outer shaft is then in particular connected to the main body in the provided manner when it is locked therein.

In the case of a medical instrument as is described here, the second transfer device in particular comprises an inner shaft, wherein the proximal end of the inner shaft is formed by a metal component, and wherein the metal component is electrically insulated from a central portion of the inner shaft.

In the case of a medical instrument as is described here, the second transfer device in particular comprises an inner shaft in the outer shaft, and the first transfer device in particular comprises a transfer rod in the inner shaft, wherein the inner shaft and the transfer rod are designed such that an electrically conductive proximal end of the inner shaft is electrically insulated in any position at least either from the outer shaft or from the transfer rod.

BRIEF DESCRIPTION OF THE DRAWINGS

Embodiments will be explained in greater detail hereinafter with reference to the accompanying figures, in which.

DETAILED DESCRIPTION OF THE INVENTION

Figure 1:
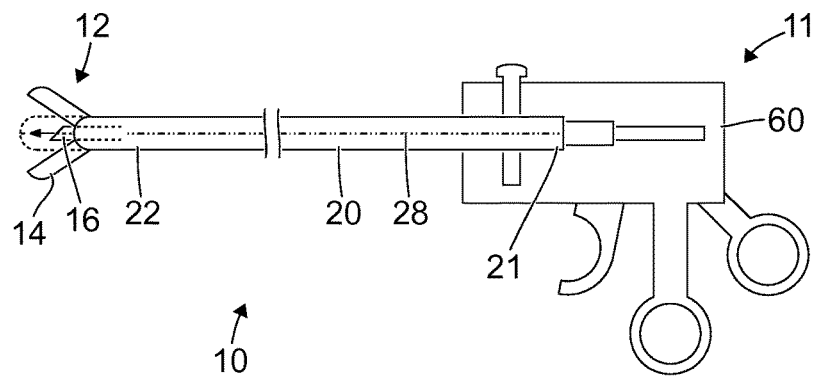
FIG. 1 shows a schematic illustration of a medical instrument.

FIG. 1 shows a schematic illustration of a medical instrument 10, comprising a proximal end 11 and a distal end 12. At the distal end 12, the medical instrument 10 has a first tool 14 and a second tool 16. The first tool 14 and the second tool 16 can be moved and used independently of one another. In the illustrated example, the first tool 14 comprises two mouth parts pivotable symmetrically with respect to one another about pivot axes perpendicular with respect to the drawing plane of FIG. 1. In the illustrated example, the second tool 16 is a scalpel, which, as is indicated by an arrow in FIG. 1, is movable between the two mouth parts of the first tool 14. The mouth parts of the first tool 14 are in particular designed such that, even in their closed positions indicated in FIG. 1 by dashed lines, a channel or a cavity in which the second tool is displaceable remains between the mouth parts of the first tool 14.

The first tool 14 is designed in particular as a bipolar electrosurgical tool. After grasping and squeezing tissue by the mouth parts of the first tool 14, a high-frequency alternating voltage can be applied between the mouth parts of the first tool 14. The tissue can thus be cauterized. Then, the tissue can be severed by means of the second tool 16.

The medical instrument 10 has at its proximal end 11 a handling device comprising a plurality of actuation devices. Exemplary embodiments of the handling devices 60 are presented below with reference to FIGS. 2 to 9.

A shaft 20 connects the handling device 60 at the proximal end 11 of the medical instrument 10 to the tools 14, 16 at the distal end 12. The shaft 20 is straight or, by contrast with the illustration in FIG. 1, curved, rigid or flexible. The shaft 20 has a longitudinal axis 28, which in particular is the axis of symmetry of the outer surface of the shaft 20. In the case of a curved shaft 20, the longitudinal axis 28 hereinafter means the longitudinal axis of the shaft 20 close to the proximal end 21 thereof.

The proximal end 21 of the shaft 20 is connected to the handling device 60, and in particular is arranged in a shaping corresponding to a recess referred to hereinafter as a coupling, where it is locked or held in an interlocked manner. The distal end 22 of the shaft 20 is connected, in particular releasably, to the first tool 14 and the second tool 16.

Figure 2:
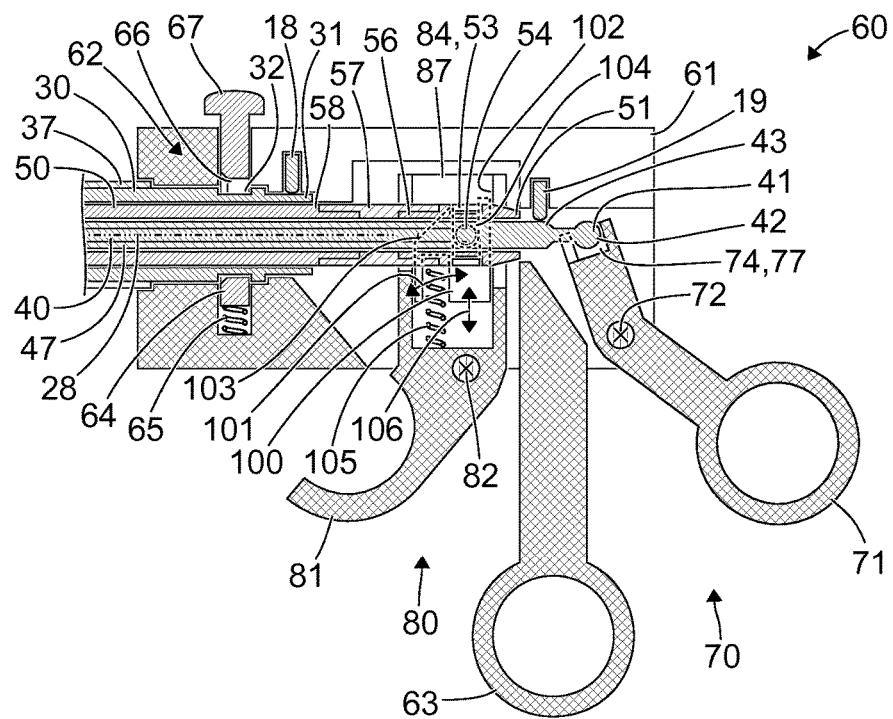
FIG. 2 shows a schematic sectional illustration of a handling device.

FIG. 2 shows a schematic illustration of a section through an exemplary embodiment of a handling device 60. The illustrated sectional plane is parallel with respect to the longitudinal axis 28 and to the drawing plane of FIG. 1. The handling device 61 can be designed so as to form together with a shaft and tools a medical instrument that has the features illustrated above with reference to FIG. 1 or other features.

The handling device 60 has a main body 61, in which a coupling 62 for the proximal end 31 of an outer shaft 30 is provided. The coupling 62 comprises a recess with shaping corresponding to the proximal end 31 of the outer shaft 30, such that the outer shaft can be introduced from the distal direction into the recess. In particular, both the proximal end 31 of the outer shaft 30 and the corresponding recess in the main body 61 are substantially rotationally symmetrical about the longitudinal axis 28.

Close to its proximal end 31, the outer shaft has a circumferential groove 32. The coupling 62 on the handling device 60 comprises a bolt 64, which is movable in a corresponding recess in the main body 61 in a direction perpendicular with respect to the longitudinal axis 28 of the outer shaft 30 and parallel with respect to the sectional plane in FIG. 2. A spring 65 slides the bolt 64 into the position illustrated in FIG. 2. The bolt 64 has a through-hole 66, of which the cross section corresponds substantially to the cross section of the outer shaft 30. At an end remote from the spring 65, the bolt 64 has a push button 67, which protrudes from the main body 61 of the handling device 60.

In the locking position of the bolt 64 illustrated in FIG. 2, the bolt 64, specifically the edge of the through-hole 66 in the bolt 64, engages into the groove 32 on the outer shaft 30. The outer shaft 30 is thus held in an interlocked manner in the position illustrated in FIG. 2, and the mechanical connection between the handling device 60 and the outer shaft 30 is locked by the bolt 64. By manually applying pressure to the push button 67, the bolt 64 can be displaced against the force of the spring 65 into an unlocking position, in which the proximal end 31 of the outer shaft 30 can be removed from the handling device 60.

In the outer shaft 30, a transfer rod 30 and an inner shaft 50 are arranged coaxially. At its proximal end 41, the transfer rod 40 comprises a ball 42. A contact region 43 with a metal surface adjoins the ball 42 distally. The contact region 43 and the ball 42 are interconnected by a neck. Distally of the contact region 43, the transfer rod 40 comprises an insulating sheath 47, which insulates the transfer rod 43 outwardly.

The inner shaft 50 is substantially tubular and is arranged in the annular gap between the transfer rod 40 and the outer shaft 30. The inner shaft 50 comprises at its proximal end 51 a ring 53 having two mutually opposed journals 54, of which one faces towards the viewer in the illustration in FIG. 2 and one is arranged on the side of the ring 53 remote from the viewer. Both journals 54 on the ring 53 are therefore arranged outside the sectional plane shown in FIG. 2, but are indicated by a dashed circular contour.

The ring 53 is mounted rotatably about the longitudinal axis 28 with little play and little friction in a corresponding groove at the proximal end 51 of the inner shaft 50. The proximal end 51 of the inner shaft with the groove receiving the ring 53 is formed by a metal component 56, which is mechanically connected via an insulator 57 to a central portion 58, likewise made of metal, of the inner shaft 50 and is electrically insulated therefrom.

The handling device 60 comprises a stationary grip part 63, which in particular is formed in one piece with the main body 61. Furthermore, the handling device 60 comprises a lever-like first actuation device 70 comprising a first grip part 71, which is mounted on the main body 61 so as to be pivotable about a first pivot axis 72 perpendicular with respect to the drawing plane in FIG. 2. The first actuation device 70, in particular the first grip part 71 of the first actuation device 70, is arranged proximally of the stationary grip part 63.

A first coupling device 74 for coupling first actuation device 70 to the transfer rod 40 is arranged at an end of the first actuation device 70 opposite the first grip part 71 based on the first pivot axis 72. A movement of the first grip part 71 distally towards the stationary grip part 63 of the handling device 60 therefore accompanies a movement of the first coupling device 74 proximally.

The first coupling device 74 is designed so as to hold the ball 42 in an interlocked manner at the proximal end 41 of the transfer rod 40 in the working position shown in FIG. 2 and in further working positions arranged further proximally. In particular, the first coupling device 74, in a sectional plane parallel with respect to the longitudinal axis 28 and parallel with respect to the first pivot axis 72, has substantially the shaping of a horseshoe or of a large Greek omega, wherein the two ends of the cross section are arranged immediately distally of the ball 42. The ball 42 is therefore also partly surrounded on its distal side by the first coupling device 74 and can be drawn proximally by the first coupling device 74.

The position of the first coupling device 74 shown in FIG. 2 will also be referred to hereinafter as the first working position 77. By means of features or devices of the handling device 60, which are not illustrated in FIG. 2, it can be ensured that the first working position 77 shown in FIG. 2 is the outermost distal position of the first coupling device 74, that is to say the first coupling device 74 cannot be pivoted further distally.

Furthermore, the handling device 60 comprises a lever-like second actuation device 80, which is arranged distally of the stationary grip part 63. The second actuation device 80 comprises a second grip part 81 and is pivotable about a second pivot axis 82 perpendicular with respect to the drawing plane of FIG. 2. The second actuation device 80 comprises a second coupling device 84 for releasable mechanical coupling of the second actuation device 80 to the proximal end 51 of the inner shaft 50. Based on the second pivot axis 82 of the second actuation device 80, the second coupling device 84 is arranged at the end of the second actuation device 80 opposite the second grip part 81.

As the second actuation device 80 is pivoted about the second pivot axis 82, the second coupling device 84 is moved over a path 101 shaped in the manner of a circular arc. In the position of the second actuation device 80 shown in FIG. 2, the second coupling device adopts a first working position 87. The first working position is the outermost proximal position of the second coupling device 84. The second coupling device 84 comprises a bolt 100. As the second actuation device 80 is pivoted about the second pivot axis 82, the bolt 100 is moved together with the second coupling device 84 over the path 101 shaped in the manner of a circular arc. Furthermore, the bolt 100 is movable relative to the second coupling device along a path 106 perpendicular with respect to the second pivot axis 82. The path 106 is defined by an interlocking linear guide 102 of the bolt 100 in the second actuation device 80. When the second actuation device 80 is pivoted about the second pivot axis 82, the path 106 is also pivoted accordingly, the bolt 100 being movable along said path relative to the second actuation device 80. In the position of the second actuation device 80 illustrated in FIG. 2, the path 106 is substantially perpendicular with respect to the longitudinal axis 28.

The bolt 100 has two sliding surfaces 103, of which one is arranged in front of the drawing plane of FIG. 2 and the other is arranged therebehind. The sliding surfaces 103 are inclined with respect to the path 106 along which the bolt 100 is movable relative to the second actuation device 80. In particular, the angle between the sliding surfaces 103 and the path 106 is between 20° and 70°. As will be presented hereinafter with reference to FIG. 5, the sliding surfaces 103 are provided and designed so as to slide against the journal 54 on the ring 53 at the proximal end 51 of the inner shaft 50.

Furthermore, the bolt 100 has two grooves 104 each for receiving a journal 54 on the ring 53 at the proximal end 51 of the inner shaft 50. One groove 104 is arranged in front on the drawing plane of FIG. 2 and the other is arranged therebehind. In the illustration in FIG. 2, each groove 104 receives one of the two journals 54. The grooves 104 are parallel or substantially parallel with respect to the path 106 along which the bolt 100 is movable relative to the second actuation device 80.

A spring 105 holds the bolt 100 in the position shown in FIG. 2 relative to the second actuation device 80. The bolt 100 can be moved along the path 106 towards the second pivot axis 82 against the force of the spring 105.

The handling device 60 further comprises a first contact device 18 and a second contact device 19, which are each illustrated in FIG. 2 as pins with rounded ends. The first contact device 18 is arranged such that, in the position of the outer shaft 30 shown in FIG. 2, it bears against the outer lateral surface of said outer shaft in the region of the proximal end 31 thereof and is thus electrically conductively connected to the outer shaft 30. The second contact device 19 is arranged such that, in the position of the transfer rod 40 shown in FIG. 2, it bears against the contact region 43 at the proximal end 41 of the transfer rod 40 and is electrically conductively contacted therewith.

The first contact device 18 and the second contact device 19 can each be pressed by means of springs or other resilient elements (not illustrated in FIG. 2) against the proximal end 31 of the outer shaft 30 or against the contact region 43 at the proximal end 41 of the transfer rod 40.

The first contact device 18 and the second contact device 19 are electrically insulated from one another, for example by means of an electrically insulating material of the main body 61 of the handling device 60. The first contact device 18 and the second contact device 19 are each electrically conductively connectable via an electrical line (not illustrated in FIG. 2) to a pole of a high-frequency high-voltage source. The potentials provided by the high-frequency high-voltage source are transferred via the first contact device 18 and the outer shaft 30 on the one hand and via the second contact device 19 and the transfer rod 40 on the other hand to two electrodes on the tool 14 (see FIG. 1), for example to the two mouth parts indicated in FIG. 1.

The insulating sheath 37 on the outer shaft 30 causes an electrical insulation from the surrounding environment, in particular from objects contacted with the outer shaft 30. The insulating sheath 47 on the transfer rod 40 ensures an electrical insulation of the transfer rod 40 from the electrically conductive central portion 58 of the inner shaft and from the outer shaft 30. The metal component 56 at the proximal end 51 of the inner shaft 50, which, in the positions of the inner shaft 50 and of the transfer rod 40 illustrated in FIG. 2, contacts the contact region 43 of the transfer rod 40, is electrically insulated from the central portion 58 of the inner shaft 50 and therefore also from the outer shaft 30 by means of the insulator 57.

Figure 3:
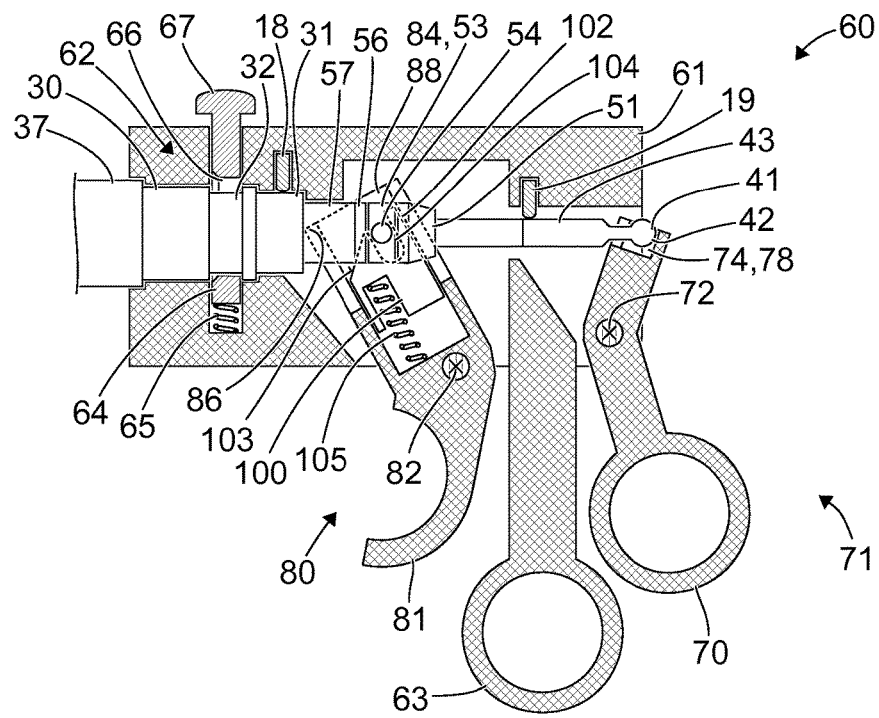
FIG. 3 shows a further schematic sectional illustration of the handling device from FIG. 2.

FIG. 3 shows a further schematic sectional illustration of the handling device 60 from FIG. 2. The illustration in FIG. 3 differs from the illustration in FIG. 2 in that merely the handling device 60 itself is illustrated in section. The outer shaft 30, the inner shaft 50 and the transfer rod 40 are by contrast shown in a corresponding side view and therefore are also considerably distinguishable from the components of the handling device 60. In FIG. 3, the groove 32 at the proximal end 31 of the outer shaft 30, into which the bolt 64 or the region of the edge of the through-hole 66 arranged close to the spring 65 engages, can be clearly seen. Furthermore, the ring 53 with the journal 54 facing towards the viewer at the proximal end 51 of the inner shaft 50 can be easily seen.

The illustration in FIG. 3 also differs from the illustration in FIG. 2 in that the transfer rod 40, the inner shaft 50, the first actuation device 70 and the second actuation device 80 adopt different positions. In particular, the first grip part 71 of the first actuation device 70 is pivoted distally, and, accordingly, the first coupling device 74 is pivoted proximally into a second working position 78, and the transfer rod 40 is displaced proximally. The outermost proximal position of the transfer rod 40 illustrated in FIG. 3 corresponds for example to the closed position of one or two pivotable mouth parts of a tool at the distal end of the shaft. Even in the proximal position of the transfer rod 40 illustrated in FIG. 3, the second contact device 19 bears against the contact region 43 at the proximal end 41 of the transfer rod 40 and thus produces an electrically conductive connection to the transfer rod 40.

In the position of the second actuation device 80 shown in FIG. 3, the second grip part 81 is pivoted proximally, and, accordingly, the second coupling device 84 is pivoted distally into a second working position 88, and the inner shaft 50 is displaced distally. In the illustrated second working position 88 of the second actuation device 80, said second actuation device, in particular a corner of the linear guides 102 arranged in front of and behind the inner shaft 50 as viewed by a viewer, bears against a proximal end face of the proximal end 31 of the outer shaft 30. When the outer shaft 30, as shown in FIGS. 2 and 3, is locked and held by the bolt 64 in the provided and illustrated position relative to the handling device 60, the second working position 88 of the second coupling device 84 is therefore the outermost distal position reachable. Accordingly, the position shown in FIG. 3 of the inner shaft 50 is the outermost distal position reachable. Even in this outermost distal position reachable of the inner shaft 50 and in the corresponding position of the second actuation device 80, the journals 54 on the ring 53 at the proximal end 51 of the inner shaft 50 within the groove 104 bear against the bolt 100 on the second actuation device 80. This signifies an interlocked coupling between the second actuation device 80 and the inner shaft 50.

Figure 4:
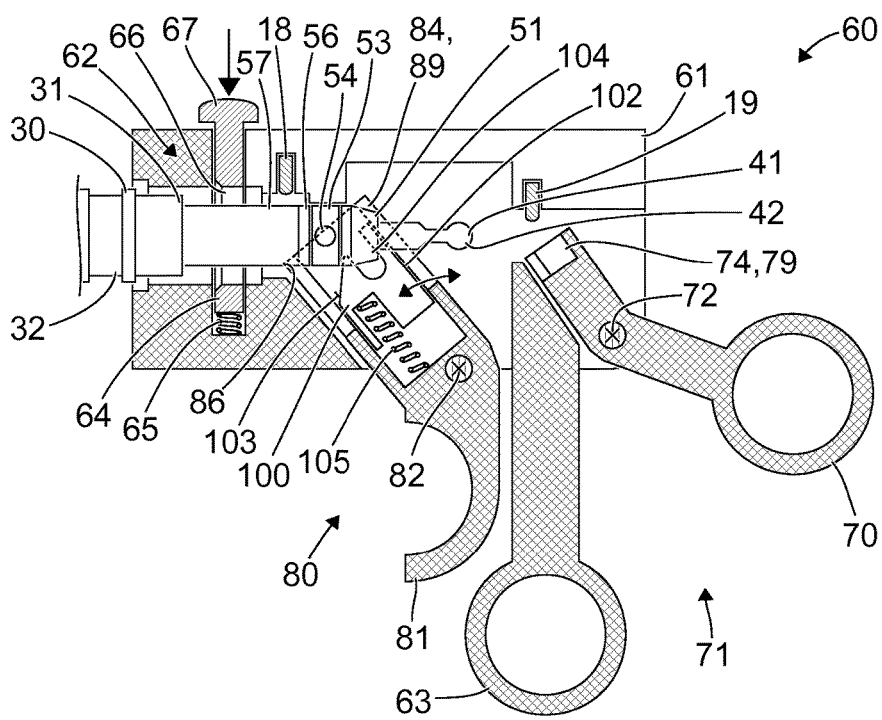
FIG. 4 shows a further schematic sectional illustration of the handling device from FIGS. 2 and 3.

FIG. 4 shows a further schematic sectional illustration of the handling device 60 from FIGS. 2 and 3. The illustration in FIG. 4 corresponds to the illustration in FIG. 3 to the extent that merely the handling device 60 is shown in section, the outer shaft 30, the transfer rod 40 and the inner shaft 50 by contrast being shown in a corresponding side view.

The illustration in FIG. 4 differs from the illustrations in FIGS. 2 and 3 in that, as a result of a force, indicated by an arrow, on the push button 67, the bolt 64 is displaced against the force of the spring 65 into an unlocking position, in which it no longer engages into the groove 32 at the proximal end 31 of the outer shaft 30, and the outer shaft 30, the inner shaft 50 and the transfer rod 40 are displaced distally and are removed in part from the handling device 60. Due to the displacement of the outer shaft 30 distally, said outer shaft, as can be seen in FIG. 3, no longer forms a stop for the second actuation device 80. The second coupling device 84 can therefore be pivoted further distally as far as the decoupling position 89 shown in FIG. 4. In the decoupling position 89 of the second actuation device 80 and of the second coupling device 84, the journals 54 on the ring 53 at the proximal end 51 of the inner shaft 50 are no longer engaged with the grooves 104 on the bolt 100 on the second actuation device 80. The inner shaft 50 can therefore also be removed distally from the handling device 60.

Due to the displacement of the outer shaft 30 distally, a displacement of the transfer rod 40 distally beyond the position shown in FIG. 2 is also possible. Here, the first coupling device 74 reaches the decoupling position 79 shown in FIG. 4, in which the ball 42 at the proximal end 41 of the transfer rod 40 is no longer connected in an interlocked manner to the first coupling device 74 on the first actuation device 70. The first actuation device 70 is in particular held in the position illustrated in FIG. 4 by a spring (not shown in FIG. 4).

The movement of the second coupling device 84 over a path 101 shaped in the manner of a circular arc corresponding to the pivoting movement of the second actuation device 80 corresponds to a displacement of the second coupling device 84 parallel with respect to the longitudinal axis 28, said displacement being superimposed by a movement of the second coupling device 84 in the direction perpendicular with respect to the longitudinal axis 28. The spacing of the second coupling device 84 from the longitudinal axis 28 thus varies during a pivoting movement of the second actuation device 80.

In the working positions 87, 88 of the second actuation device 80 illustrated in FIGS. 2 and 3, the second coupling device 84 has a maximum spacing from the longitudinal axis 28 achieved in the position shown in FIG. 3, wherein the journals 54 on the ring 53 at the proximal end 51 of the inner shaft are still engaged with the grooves 104 on the bolt 100 on the second actuation device 80. By contrast, in the decoupling position 89 of the second coupling device 84 shown in FIG. 4, the spacing between the second coupling device 84 and the longitudinal axis 28 is so large that the journals 54 on the ring 53 at the proximal end 51 of the inner shaft 50 are no longer engaged with the grooves 104 on the bolt 100 of the second actuation device 80.

Figure 5:
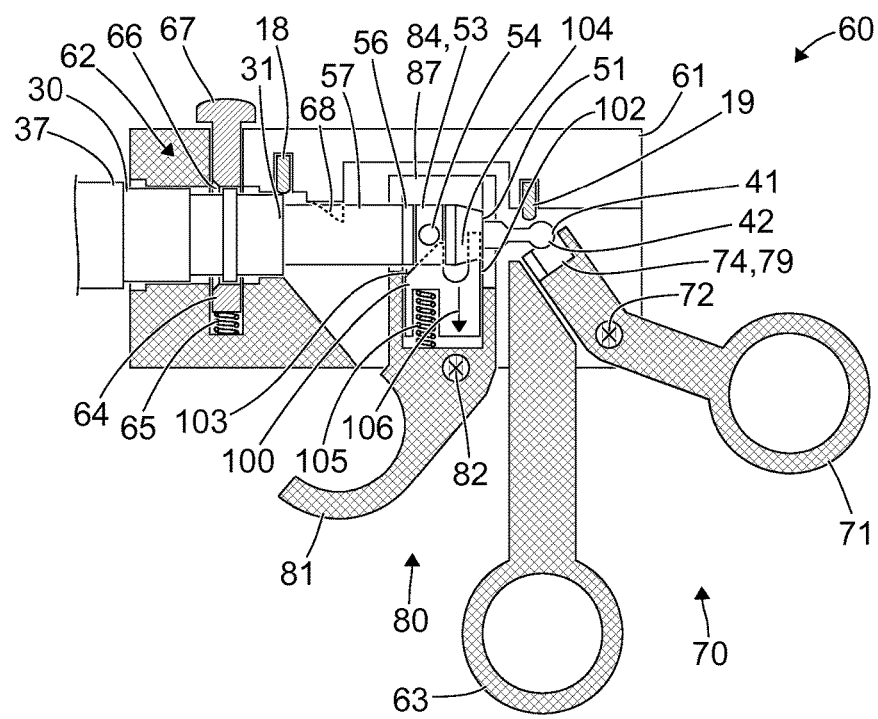
FIG. 5 shows a further schematic sectional illustration of the handling device from FIGS. 2 to 4.

FIG. 5 shows a further schematic sectional illustration of the handling device 60 from FIGS. 2 to 4. The illustration in FIG. 5 corresponds to the illustrations in FIGS. 3 and 4 in so far as merely the handling device 60 is illustrated in section, but by contrast the outer shaft 30, the inner shaft 50 and the transfer rod 40 are illustrated in a corresponding side view.

FIG. 5 shows the handling device 60, the outer shaft 30, the inner shaft 50 and the transfer rod 40 in positions or in a configuration as may be temporarily provided when inserting the outer shaft 30, the inner shaft 50 and transfer rod 40 into the handling device 60 from a distal direction in a proximal direction. Due to the springs (not shown in FIGS. 2 to 5) already mentioned above in the description of FIG. 4, the first actuation device 70 is held in the decoupling position 79 already shown in FIG. 4, in which the first coupling device 74 on the first actuation device 70 can receive the ball 42 at the proximal end 41 of the transfer rod 40.

As the inner shaft 50 is inserted into the handling device 60, the ring 53 with the journals 54 at the proximal end 51 of the inner shaft 50 can adopt any position based on the possible rotation about the longitudinal axis 28. Due to an orientation device 68, the ring 53 with the journals 54 is oriented into the position shown in FIG. 5 as the inner shaft 50 is inserted into the handling device 60. The orientation device 68 has two sliding surfaces or sliding edges, which are arranged in a wedge-shaped or V-shaped manner, extend along the outer lateral surface of the inner shaft 50, and along which one of the two journals 54 slides until the ring 53 with the journals 54 adopts the provided position shown in FIGS. 2 to 5.

In contrast to the first actuation device 70, the second actuation device 80 can adopt an arbitrary position when the outer shaft 30 is inserted with the inner shaft 50 and the transfer rod 40. If the second actuation device 80 randomly adopts the decoupling position 89 shown in FIG. 4, the journals 54 and the ring 53 at the proximal end 51 of the inner shaft 50 can be received directly into the grooves 104 on the bolt 100 on the second actuation device 80. If the second actuation device 80 initially adopts the second working position 88 shown in FIG. 3 or a position between the working positions 87, 88 shown in FIGS. 2 and 3, the journals 54 on the ring 53 initially contact the sliding surfaces 103 on the bolt 100. As the inner shaft 50 is moved proximally, the second coupling device 84 is thus initially pivoted into the outermost proximal first working position 87 shown in FIG. 5. When the second coupling device 84 on the second actuation device 80 has reached the first working position 87, a further movement of the inner shaft 50 proximally causes a displacement of the bolt 100 along the path 106 against the force of the spring 105 into the position shown in FIG. 5 and also further towards the second pivot axis 82 due to the incline of the sliding surfaces 103 on the bolt 100, against which the journals 54 slide.

When the inner shaft 50 is displaced from the position shown in FIG. 5 slightly further proximally and the bolt 100 is thus displaced against the force of the spring 105 slightly further towards the second pivot axis 82, the journals 54 reach into the grooves 104 in the bolt 100, the spring 105 moves the bolt 100 away from the second pivot axis 82 into the locking position shown in FIG. 2, and the interlocked mechanical coupling between the inner shaft 50 on the one hand and the bolt 100 and the second actuation device 80 on the other hand is produced.

Figure 6:
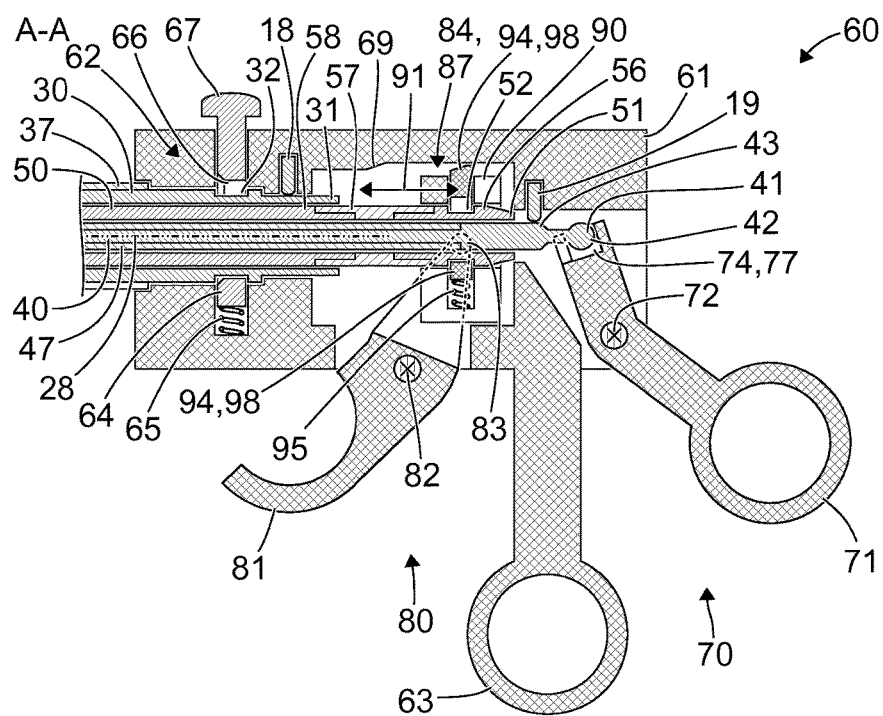
FIG. 6 shows a schematic sectional illustration of a further handling device.

FIG. 6 shows a schematic sectional illustration of a further handling device 60, which is similar in terms of some features to the handling device presented above with reference to FIGS. 2 to 5. The illustration in FIG. 6 corresponds to the illustration in FIG. 2, in particular in terms of the sectional plane and in terms of the type of illustration of the outer shaft 30, of the inner shaft 50 and of the transfer rod 40.

The handling device 60 illustrated in FIG. 6 differs from the handling device presented above with reference to FIGS. 2 to 5 in particular in terms of the features of the second coupling device 84. In a manner corresponding to the different features of the second coupling device 84 of the handling device 60, the proximal end 51 of the inner shaft 50 also has different features compared to the example presented above with reference to FIGS. 2 to 5.

The second coupling device 84 and the second actuation device 80 comprises a carriage 90, which is mechanically coupled to the second actuation device 80, but is not rigidly connected thereto. The carriage 90 is movable along a straight path 91 parallel with respect to the longitudinal axis 28. The straight path 91 is defined by features of the carriage 90 and of the main body 61 of the handling device 60, which are described below with reference to FIGS. 7 and 9. The mechanical coupling between the second actuation device 80 and the carriage 90 of the second coupling device 84 is achieved by features likewise described below with reference to FIGS. 7 and 9. As a result, a pivoting of the second actuation device 80 about the second pivot axis 82 accompanies a movement of the second coupling device 84, in particular of the carriage 90, along the straight path 91.

The carriage 90 has a bolt 94, which is movable in a corresponding recess in the carriage 90 in a direction perpendicular with respect to the longitudinal axis 28 and perpendicular with respect to the path 91. The bolt 94, in particular similarly to the bolt 64 of the coupling 62 for the outer shaft 30, has substantially the design of a plate with a through-hole, wherein the cross section of the through-hole corresponds to the cross section of the inner shaft 50. Similarly to the handling device presented above with reference to FIGS. 2 to 5, the metal component 56 at the proximal end 51 of the inner shaft 50 has a groove, but no ring in the groove. A spring 95 slides the bolt 94 within the carriage 90 into the position shown in FIG. 6, in which a region of the edge of the through-hole in the bolt 94 engages into the groove 52 at the proximal end 51 of the inner shaft 50. In this position, the bolt 94 engaging into the groove 52 forms an interlocked and, apart from unavoidable play, mechanically rigid connection between the carriage 90 or the second coupling device 84 on the one hand and the proximal end 51 of the inner shaft 50 on the other hand.

FIG. 6 shows the first coupling device 74 and the second coupling position 84 in first working positions 77, 87. Due to features or devices of the handling device 60, which are not illustrated in FIG. 6, it can be ensured that the first working position 77, shown in FIG. 6, of the first coupling device 74 is the outermost distal position of the first coupling device 74, that is to say the first coupling device 74 cannot be pivoted further distally. Due to features or devices of the handling device 60, which are not illustrated in FIG. 2, in particular due to a mechanical stop on the main body 61 for the carriage 90, it can be ensured that the first working position 87, shown in FIG. 6, of the second coupling device 84, is the outermost proximal position of the second coupling device 84, that is to say the second coupling device 84 cannot be pivoted further distally.

Figure 7:
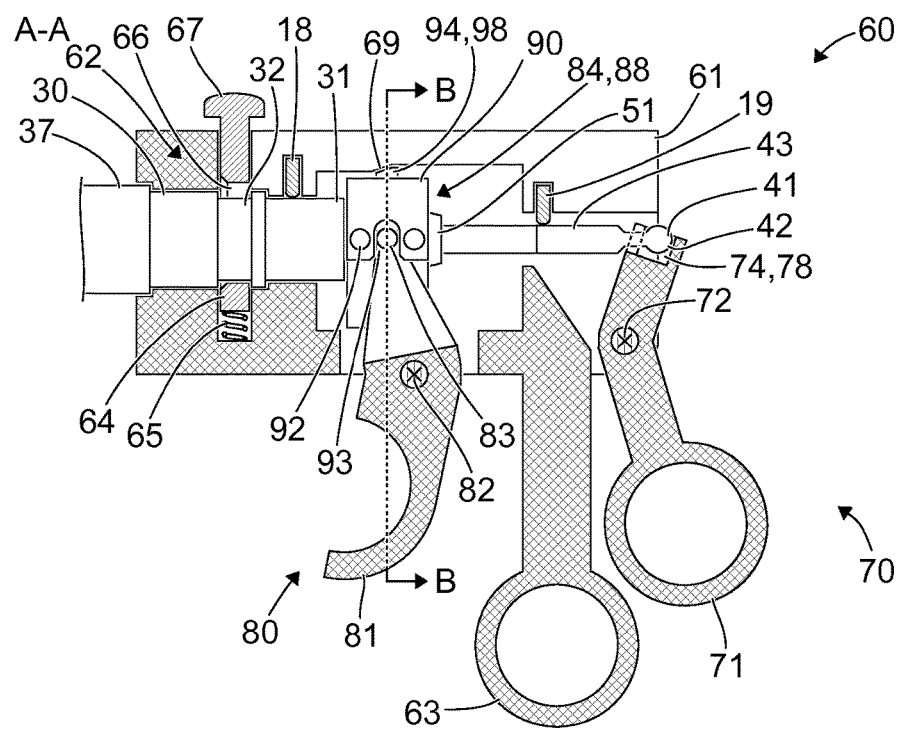
FIG. 7 shows a further schematic sectional illustration of the handling device from FIG. 6.

FIG. 7 shows a further schematic illustration of the handling device 60 from FIG. 6, which is similar to that in FIG. 3 in terms of the type of illustration. In particular, the handling device 60 is shown substantially in section and the outer shaft 30, the inner shaft 50 and the transfer rod 40 are shown in a corresponding side view. By contrast however, the second coupling device 84, in particular the carriage 90, likewise counting towards the handling device 60, is not illustrated in section, but in a side view. The illustration in FIG. 7 also corresponds substantially in terms of the positions of the first actuation device 70, the second actuation device 80, the transfer rod 40 and the inner shaft 50 to the illustration in FIG. 3. In particular, the first coupling device 74 adopts a second working position 78, which is the outermost proximal position reachable of the first coupling device 74. Furthermore, the second coupling device 84 adopts a second working position 88, which is the outermost distal position reachable of the second coupling device 84.

In FIG. 7, two guide pins 92 are visible on the side of the carriage 90 facing towards the viewer and engage into a corresponding groove (not illustrated in FIG. 7) in the main body 61 of the handling device 60. Two further guide journals (not visible in FIG. 7) on the side of the carriage 90 facing away from the viewer engage into a corresponding further groove in the main body 61 of the handling device 60, symmetrically about the sectional plane of FIG. 7. The guide journals 92 and the grooves in the main body 61 of the handling device 60 define the path 91 (see FIG. 6) along which the carriage 90 is movable.

A journal 83 at an end, remote from the second grip part 81, of the second actuation device 80 engages into a corresponding groove 93 on the carriage 90. The groove 93 on the carriage 90 extends substantially perpendicular with respect to the path 91 (see FIG. 6) along which the carriage 90 is movable. A further journal engages into a further groove on the side of the carriage 90 facing away from the viewer, symmetrically about the sectional plane of FIG. 7. The journals 83 on the second actuation device 80 and the grooves 93 on the carriage 90 couple the second actuation device 80 in the above-described manner mechanically to the carriage 90.

In the second working position 88 of the second coupling device 84, in particular of the carriage 90, shown in FIG. 7, a distal end face of the carriage 90 bears against a proximal end face of the proximal end 31 of the outer shaft 30. When the outer shaft 30 is locked in the handling device 60, as illustrated in FIGS. 6 and 7, the second working position shown in FIG. 7 of the second coupling device 84 and of the carriage 90 thus constitutes the outermost distal position reachable.

Figure 8:
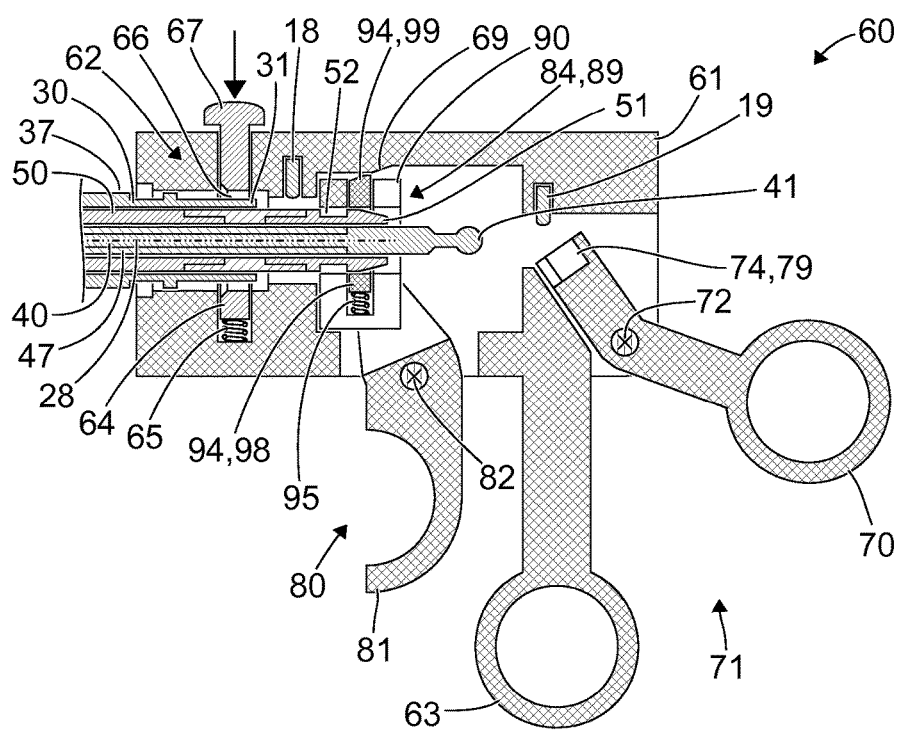
FIG. 8 shows a further schematic sectional illustration of the handling device from FIGS. 6 and 7.

FIG. 8 shows a further schematic sectional illustration of the handling device from FIGS. 6 and 7. With regard to the type of illustration, FIG. 8 corresponds to FIG. 6. In particular, both the handling device 60 including the second coupling device 84 and also the outer shaft 30, the inner shaft 50 and the transfer rod 40 are illustrated in section.

The illustration in FIG. 8 differs from the illustrations in FIGS. 6 and 7 in particular in that the bolt 64 on the coupling 62 is displaced by a force indicated by an arrow against the force of the spring 65 into the position shown in FIG. 8, in which said bolt does not engage into the groove 32 at the proximal end 31 of the outer shaft 30. In this unlocking position of the bolt 64, the outer shaft 30, the inner shaft 50 and the transfer rod 40 can be removed distally from the handling device 60. Here, FIG. 8 shows by way of example the temporarily adopted positions of the outer shaft 30, of the inner shaft 50 and of the transfer rod 40.

When the outer shaft 30 no longer adopts the position shown in FIGS. 6 and 7, in which it is mechanically connected and locked to the main body 61 of the handling device 60, the second coupling device 84 can be displaced further distally beyond the second working position 88 shown in FIG. 7 and as far as the decoupling position 89 shown in FIG. 8. Here, an end of the bolt 94 remote from the spring 95 is displaced by a ramp-shaped region 69 on the main body 61 of the handling device 60 against the force of the spring 95 from a working position 98 (see FIG. 7) into the unlocking position 99 shown in FIG. 8, in which the bolt 94 no longer engages into the groove 52 at the proximal end 51 of the inner shaft 50. The proximal end 51 of the inner shaft 50, as indicated in FIG. 8, can then be removed distally from the second coupling device 84 and in particular from the carriage 90.

Similarly to the exemplary embodiment in FIGS. 2 to 5, a mechanical connection between the proximal end 51 of the inner shaft 50 and the second coupling device 84 or the carriage 90 can be produced in any position of the carriage 90. Here, the carriage 90 in particular is initially displaced into its outermost proximal position shown in FIG. 6. A conical region at the proximal end 51 of the inner shaft 50 then deflects the bolt 94 against the force of the spring 95 until the bolt 94 engages into the groove 52 at the proximal end 51 of the inner shaft 50.

Figure 9:
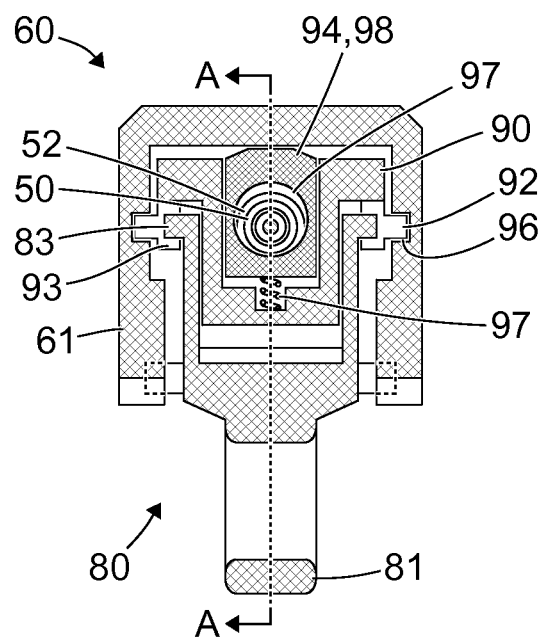
FIG. 9 shows a further schematic sectional illustration of the handling device from FIGS. 6 to 8.

FIG. 9 shows a further schematic sectional illustrational of the handling device from FIGS. 6 to 8. A section along the plane B-B, which is indicated in FIG. 7, is shown. The position and orientation of the sectional plane A-A in FIGS. 6 to 8 is indicated in FIG. 9. The sectional plane B-B is perpendicular with respect to the longitudinal axis 28 and perpendicular with respect to the sectional plane A-A.

In FIG. 9, a fork-shaped design of the second actuation device 80 at its end distanced from the second grip part 81, the pins 83 formed on the second actuation device 80 and engaging into grooves or slits 93 on the carriage 90, the guide pins 92 on the carriage 90, the corresponding grooves in the main body 61 of the handling device 60, the plate-shaped design of the bolt 94, and the through-hole 97 in the bolt 94 for the inner shaft 50 can be seen. The bolt 94 is illustrated in the working position 98, in which it is located when the second coupling device 84 and the carriage 90 are located in one of the working positions 87, 88.

REFERENCE SIGNS 10 medical instrument
11 proximal end of the medical instrument 10
12 distal end of the medical instrument 10
14 first tool at the distal end 12 of the medical instrument 10
16 second tool at the distal end 12 of the medical instrument 10
18 first contact device
19 second contact device
20 shaft of the medical instrument 10
21 proximal end of the shaft 20
22 distal end of the shaft 20
28 longitudinal axis of the shaft 20
30 outer shaft
31 proximal end of the outer shaft 30
32 groove at the proximal end 31 of the outer shaft 30
37 insulating sheath on the outer shaft 30
40 transfer rod
41 proximal end of the transfer rod 40
42 ball at the proximal end 41 of the transfer rod 40
43 contact region at the proximal end 41 of the transfer rod 40
47 insulating sheath on the transfer rod 40
50 inner shaft
51 proximal end of the inner shaft 50
52 groove at the proximal end 51 of the inner shaft 50

53 ring at the proximal end 51 of the inner shaft 50
54 journal on the ring 53
56 metal component at the proximal end 51 of the inner shaft 50
57 insulator between metal component 56 and central portion 58
58 central portion of the inner shaft 50
60 handling device at the proximal end 11 of the medical instrument 10
61 main body of the handling device 60
62 coupling for proximal end 31 of the outer shaft 30
63 stationary grip part on the handling device 60
64 bolt on the coupling 62
65 spring on the bolt 64
66 through-hole in the bolt 64
67 push button on the bolt 64
68 orientation device for journal 54
69 ramp-shaped region on the main body 61
70 first actuation device on the handling device 20
71 first grip part on the first actuation device 70
72 first pivot axis of the first actuation device 70
74 first coupling device for coupling the first actuation device 70 to the first transfer device 40
77 first working position of the first coupling device 74
78 second working position of the first coupling device 74
79 decoupling position of the first coupling device 74
80 second actuation device on the handling device 20
81 second grip part on the second actuation device 80
82 second pivot axis of the second actuation device 80
83 pin for mechanical coupling to the carriage 90
84 second coupling device for coupling of the second actuation device 80 to the second transfer device 50
85 coupling position or region of coupling positions
86 corner of the second actuation device 80
87 first working position of the second coupling device 84
88 second working position of the second coupling device 84
89 decoupling position of the second coupling device 84
90 carriage on the second coupling device 84
91 path along which the carriage 90 is movable
92 guide pin on the carriage 90
93 groove for the pin 83 on the second actuation device 80
94 bolt on the second coupling device 84
95 spring on the bolt 94
96 groove on the main body 61 for the guide pin 92 on the carriage 90
97 through-hole
98 working position of the bolt 94
99 unlocking position of the bolt 94
100 bolt on the second coupling device 84
101 path along which the bolt 100 is movable with the second actuation device 80
102 interlocked linear guide of the bolt 100 on the second actuation device 80
103 sliding surface on the bolt
104 groove for the journal 54 on the ring 53 at the proximal end 53 of the inner shaft 50
105 spring on the bolt 100
106 path along which the bolt 100 is movable relative to the second actuation device 80

The invention claimed is:

1. A handling device for a medical instrument, comprising:
a main body with a coupling configured to releasably connect to a proximal end of an outer shaft;
a first actuation device, which is movable relative to the main body;
a second actuation device, which is movable relative to the main body;
a first coupling device configured to couple the first actuation device to a first transfer device so as to transfer at least one of a force and a torque; and
a second coupling device configured to couple the second actuation device to a second transfer device so as to transfer at least one of a force and a torque;
wherein the first coupling device has a decoupling position in which the first actuation device is decoupled from the first transfer device, and the second coupling device has a decoupling position in which the second actuation device is decoupled from the second transfer device; and
wherein the first coupling device is configured such that the decoupling position of the first coupling device can only be reached when the outer shaft is not connected to the coupling on the main body, and the second coupling device is configured such that the decoupling position of the second coupling device can only be reached when the outer shaft is not connected to the coupling on the main body.

2. The handling device according to claim 1, wherein the second coupling device is electrically insulated in any position from at least one of: (i) the proximal end of the outer shaft when connected to the main body of the handling device; and (ii) a proximal end of the first transfer device when coupled to the first actuation device.

3. The handling device according to claim 1, wherein the first actuation device is configured to open and close mouth parts of a first tool, and the second actuation device is configured to move a second tool at a distal end of a shaft to be coupled to the handling device.

4. The handling device according to claim 1, wherein the first actuation device is arranged proximally of a stationary grip part of the handling device, and the second actuation device is arranged distally of the stationary grip part.

5. The handling device according to claim 1, wherein the second coupling device includes a carriage, which is displaceable by the second actuation device along a predetermined path.

6. The handling device according to claim 5, wherein the second coupling device includes a bolt for holding a proximal end of the second transfer device in an interlocked manner on the carriage; and
wherein the main body is configured such that, as the second coupling device approaches the decoupling position, the main body moves the bolt into an unlocking position, in which the bolt no longer holds the proximal end of the second transfer device in the interlocked manner.

7. The handling device according to claim 6, wherein the carriage is movable in a first direction; and
wherein the bolt is movable relative to the carriage in a second direction perpendicular with respect to the first direction.

8. The handling device according to claim 1, wherein the second coupling device is movable by the second actuation device along a curved path.

9. The handling device according to claim 8, wherein an interlocked coupling of the second coupling device to the second transfer device is dependent on a spacing between the second coupling device and a longitudinal axis of the second transfer device;

wherein the decoupling position of the second coupling device over the curved path is distanced so far from the longitudinal axis that there is no coupling between the second coupling device and the second transfer device; and wherein other positions of the second coupling device are arranged so close to the longitudinal axis that an interlocked coupling of the second coupling device to the second transfer device may be present.

10. The handling device according to claim 8, wherein the second coupling device includes a bolt;
wherein the bolt is displaceable along the curved path by actuation of the second actuation device; and
wherein the bolt is movable relative to the second actuation device along a further path, which is substantially perpendicular with respect to the curved path.

11. The handling device according to claim 10, wherein the bolt is movable out of a working position, relative to the second actuation device along the further path against a resilient force of a resilient element; and
wherein the bolt has a sliding surface, which is inclined with respect to the curved path and with respect to the further path, and is configured such that a proximal end, introduced into the handling device, of the second transfer device can slide the bolt along the further path at the sliding surface.

12. The handling device according to claim 1, wherein the coupling of the main body includes a bolt movable in a corresponding recess in the main body, between a locking position and an unlocking position, and in a direction perpendicular to a longitudinal axis of the outer shaft when the outer shaft is connected to the coupling; and
wherein the bolt is configured such that: (i) in the locking position, the bolt interlockingly engages the proximal end of the outer shaft when the proximal end of the outer shaft is connected to the coupling; and (ii) in the unlocking position, the bolt does not engage the proximal end of the outer shaft.

13. The handling device according to claim 12, wherein the decoupling position of the first coupling device can only be reached when the bolt is in the unlocking position, and the decoupling position of the second coupling device can only be reached when the bolt is in the unlocking position.

14. A medical instrument, comprising:
an outer shaft;
a first transfer device in the outer shaft;
a second transfer device in the outer shaft; and
a handling device having:
a main body with a coupling configured to releasably connect to a proximal end of the outer shaft;
a first actuation device, which is movable relative to the main body;
a second actuation device, which is movable relative to the main body;
a first coupling device configured to couple the first actuation device to the first transfer device so as to transfer at least one of a force and a torque;
a second coupling device configured to couple the second actuation device to the second transfer device so as to transfer at least one of a force and a torque;
wherein the first coupling device has a decoupling position in which the first actuation device is decoupled from the first transfer device, and the second coupling device has a decoupling position in which the second actuation device is decoupled from the second transfer device; and
wherein the first coupling device is configured such that the decoupling position of the first coupling device can only be reached when the outer shaft is not connected to the coupling on the main body, and the second coupling device is configured such that the decoupling position of the second coupling device can only be reached when the outer shaft is not connected to the coupling on the main body.

15. The medical instrument according to claim 14, wherein the proximal end of the outer shaft prevents the second coupling device from reaching its decoupling position when the outer shaft is connected to the main body.

16. The medical instrument according to claim 14, wherein the second transfer device includes an inner shaft, wherein a proximal end of the inner shaft is formed by a metal component that is electrically insulated from a central portion of the inner shaft.

17. The medical instrument according to claim 14, wherein the second transfer device includes an inner shaft in the outer shaft;
wherein the first transfer device includes a transfer rod in the inner shaft; and
wherein the inner shaft and the transfer rod are configured such that an electrically conductive proximal end of the inner shaft is electrically insulated in any position from at least one of: (i) the outer shaft; and (ii) the transfer rod.

18. The medical instrument according to claim 14, wherein the coupling of the main body includes a bolt movable in a corresponding recess in the main body, between a locking position and an unlocking position, and in a direction perpendicular to a longitudinal axis of the outer shaft when the outer shaft is connected to the coupling;
wherein the bolt is configured such that: (i) in the locking position, the bolt interlockingly engages the proximal end of the outer shaft when the proximal end of the outer shaft is connected to the coupling; and (ii) in the unlocking position, the bolt does not engage the proximal end of the outer shaft; and
wherein the decoupling position of the first coupling device can only be reached when the bolt is in the unlocking position, and the decoupling position of the second coupling device can only be reached when the bolt is in the unlocking position.

* * * * *